US005705709A

United States Patent [19]
Guettes et al.

[11] Patent Number: 5,705,709
[45] Date of Patent: Jan. 6, 1998

[54] PREPARATION OF BROMINE-CONTAINING POLYOLS

[75] Inventors: Bernd Guettes, Sallgast; Regina Pretzsch, Schipkau; Ralf Fritz, Schwarzheide, all of Germany

[73] Assignee: BASF Schwarzheide GmbH, Schwarzheide, Germany

[21] Appl. No.: 548,989

[22] Filed: Oct. 27, 1995

[30] Foreign Application Priority Data

Nov. 10, 1994 [DE] Germany .................. 44 40 213.9

[51] Int. Cl.$^6$ .................................................. C07C 43/02
[52] U.S. Cl. ............................................................. 568/614
[58] Field of Search ................................................ 568/614

[56] References Cited

U.S. PATENT DOCUMENTS

| 4,657,964 | 4/1987 | Lai et al. | 524/409 |
| 5,034,423 | 7/1991 | Blount | 521/107 |

Primary Examiner—Marianne M. Cintins
Assistant Examiner—Dwayne C. Jones
Attorney, Agent, or Firm—Fernando A. Borrego

[57] ABSTRACT

The invention relates to a process for the preparation of bromine-containing polyols in which a bromine-containing alcohol is caused to react with an alkylene oxide in admixture with other H-functional compounds and the catalyst used is a system comprising alkaline and Lewis-acid catalysts.

19 Claims, No Drawings

PREPARATION OF BROMINE-CONTAINING POLYOLS

The invention relates to a process for the preparation of bromine-containing polyols, which are particularly suitable for use as flame-retardants for polyurethanes.

The use of bromine-containing alcohols and polyols as flame-retardants for polyurethanes has been known for many years and is described in the literature in many places.

The use of such products has the advantage of affording good flame-retarding action but it also gives rise to a number of problems. A significant drawback of the products of the prior art resides is their poor miscibility with the other starting materials of the polyol components.

For example, dibromobutanediol precipitates as solids rapidly from the polyol mixtures and reacts very slowly with the isocyanate components.

A number of proposals has been offered for overcoming this drawback. Thus a proposal made in U.S. Pat. No. 3,933,690 is to cause polyether alcohols to react with dibromobutenediol under acid catalysis at temperatures near 70° C. However this linkage reaction causes scissions in polyether alcohols. In addition, this results in evolution of bromine and intense darkening of the reaction products.

GB-A 1,412,384 and EP-B 0,221,586 describe the preparation of bromine-containing polyols by the reaction of butenediol or butynediol with epichlorohydrin and/or other alkylene oxides and bromination of the unsaturated polyols produced. However this process produces only polyols having low contents of bromine and showing poor functionality, the use of which is only possible in hard polyurethane foams at the expense of quality.

U.S. Pat. No. 3,474,148 describes the preparation of bromine-containing monoalkyl ethers of trimethylolpropane or pentaerythritol by brominating the corresponding allyl ethers. However the preparation of allyl ethers is a slow reaction which is difficult to control. In addition the subsequent bromination produces a number of side reactions involving a large number of reaction products.

Another possibility is the process described in DD-A 207,916, in which polyols are caused to react with formaldehyde and dibromobutenediol. This process however usually causes an undesirable increase in the viscosity of the alcohols. In addition, the reaction is difficult to control and segregations and incompatibilities can be the result when the resulting products are used in polyurethane systems.

Another variant of this process is described in DE-A 2,166,942, where bromine-containing alcohol components are caused to react with carboxylic acids to produce esters. Such products cannot be used in all polyurethane systems, however.

It is the object of the invention to provide a process for the preparation of bromine-containing polyols, in which side reactions and evolution of bromine are substantially suppressed and which yields products of low viscosity and high functionality and exibiting good compatibility in polyurethane systems.

We have been able to achieve the object of the invention, surprisingly, by means of a process for the preparation of bromine-containing polyols, wherein a bromine-containing alcohol is caused to react with an alkylene oxide together with other H-functional, in particular hydroxy-functional, compounds and the catalyst used is a system comprising alkaline and Lewis-acid catalysts.

The bromine-containing alcohols used are, in particular, aliphatic saturated and/or unsaturated alcohols having from 2 to 10 carbon atoms and a branched or unbranched carbon chain or brominated phenols. Preferred representatives are dibromoneopentyl alcohol, tribromoneopentyl alcohol, dibromobutanediol, dibromobutenediol, and mono-, di-, and tri-bromophenols.

The hydroxy-functional compounds which are caused to react with alkylene oxides in accordance with the present invention together with the bromine-containing alcohols may advantageously be those representatives thereof as are usually employed in polyurethane chemistry as starting substances for polyether alcohols, for example low molecular weight polyfunctional alcohols and sugar alcohols. An alternative method is to cause reaction products of such compounds with alkylene oxides to react with alkylene oxides together with the bromine-containing alcohols. In this case it may be advantageous to use unneutralized products in which radicals of the alkaline alkoxylation catalyst are still present.

The alkaline catalysts used are the alkali metal and alkaline earth metal hydroxides and carbonates usually employed for the preparation of polyether alcohols by reaction of H-functional compounds with alkylene oxides. When use is made of unneutralized alkylene oxide adducts as hydroxy-functional compounds the action of the catalyst residues present therein can be sufficient for the process of the invention, so that the addition of extra catalyst is no longer necessary.

The Lewis-acid catalyst used are, in particular, halides of Group IIIa elements, for example aluminum chloride or boron fluoride. When use is made of the preferred boron fluoride this is usually used in the form of complexes with organic ligands for ease of handling, for example as ethyl ether complex.

The alkylene oxides used are the lower alkylene oxides commonly used for the preparation of polyether alcohols, in particular ethylene oxide and/or propylene oxide. The chemical addition of the alkylene oxides can be carried out to form block or random polymers in this process, depending on the desired composition of the end product, in the usual manner.

To this end it is advantageous, particularly when use is made of a solid hydroxy-functional compound, to prepare a homogeneous mixture of said compound with the bromine-containing alcohol and then to add the catalyst thereto. An alternative method is to form a homogeneous mixture of all components.

The process of the invention is carried out in pressure vessels.

Before metering in the alkylene oxide it is advantageous to inert the mixture by means of inert gas, preferably nitrogen.

The reaction of the mixture of starting substances prepared as described above with the alkylene oxides is carried out under the reaction conditions usually employed for the alkoxylation of H-functional starting substances, such as temperatures of from 50° to 140° C. and pressures of from 2 to 6 bar. The catalyst is then removed. This takes place by neutralization with acid and filtration of the salts formed and the boron trifluoride.

Water and readily volatile components are then removed from the bromine-containing polyol. This is usually carried out by vacuum distillation.

The process of the invention can be carried out in a straighforward manner in any conventional polyether alcohol plant. Due to the complex catalysis there is hardly any occurrence of side reactions or evolution of bromine. The bromine-containing polyols produced by the process of the invention are homogeneous, low-viscosity clear liquids.

They are readily miscible in the usual polyurethane systems. Due to the fact that it is possible to use co-starters of higher functionality, products of high functionality can also be prepared which are very well suited for incorporation in hard polyurethane foam systems, in particular.

The bromine-containing polyols produced by the process of the invention can be used in polyurethane systems alone or in conjunction with other flame-retardants.

By combining different starting products the process of the invention makes it possible to adapt the flame-retardants in a precise manner to the target polyurethanes.

The invention is illustrated below with reference to the following examples:

EXAMPLE 1

(for comparison)

130 g of dibromoneopentyl glycol, 90 g of sorbitol, and 5 g of 45% strength aqueous potassium hydroxide solution were fed into an autoclave having a capacity of 1 L, purged with nitrogen and heated to 110° C. At this temperature, 400 g of propylene oxide were metered in over a period of 100 min and caused to react. The metered introduction of alkylene oxide was followed by a post reaction phase lasting 30 min at 110° C. The basic catalyst was then neutralized by the addition of 30 g of water and 2.3 g of 85% strength aqueous phosphoric acid. The crude polyether alcohol obtained was distilled at 110° C. and a pressure of less than 10 mbar and then filtered.

The polyether alcohol obtained was inhomogeneous and could not be incorporated in polyurethane systems. During the reactions evolution of bromine took place. The polyether alcohol had the following specifications:
hydroxyl number: 350 mgKOH/g
viscosity at 25° C.: 600 mPas
acid number: 3.43 mgKOH/g
pH: 1.87
bromine content: 8.6 wt %, based on the polyether alcohol

EXAMPLE 2

(for comparison)

130 g of dibromoneopentyl glycol, 117 g of saccharose, and 5 g of 45% strength aqueous potassium hydroxide solution were fed into an autoclave having a capacity of 1 L, purged with nitrogen and heated to 110° C. At this temperature, 420 g of propylene oxide were metered in over a period of 100 min and caused to react. The metered introduction of alkylene oxide was followed by a post reaction phase lasting 45 min at 110° C. The basic catalyst was then neutralized by the addition of 35 g of water and 2.5 g of 85% strength aqueous phosphoric acid. The crude polyether alcohol obtained was distilled at 110° C. and a pressure of less than 10 mbar and then filtered.

The polyether alcohol obtained was inhomogeneous and still contained unconverted portions of starter molecules. It could not be incorporated in polyurethane systems. During the reactions evolution of bromine took place. The polyether alcohol had the following specifications:
hydroxyl number: indeterminable due to inhomogeneity
viscosity at 25° C. (liquid phase): 800 mPas
acid number (liquid phase): 6.17 mgKOH/g
pH: 1.19
bromine content: 5.9 wt %, based on the polyether alcohol

EXAMPLE 3

260 g of dibromoneopentyl glycol and 290 g of a reaction product of 182 g of sorbitol, 30 g of water, and 1.9 g of 45% strength aqueous potassium hydroxide solution with 140 g of propylene oxide were fed into an autoclave having a capacity of 1 L. The propylene oxide reaction product had an alkalinity, stated in terms of $K^+$ ions, of 2000 ppm. At this temperature 300 g of propylene oxide were added. Following the aklylene oxide feed and a 30 minute post reaction phase the crude polyether alcohol was purified by the addition of 40 g of water and 0.1 g of 85% strength aqueous phosphoric acid and worked up. The polyether alcohol thus obtained was homogeneous and could be incorporated in conventional polyurethane systems without difficulty. It had the following specifications:
hydroxyl number: 345 mgKOH/g
viscosity at 25° C.: 2820 mPas
acid number: 0.47 mgKOH/g
pH: 6.3
bromine content: 13.9 wt %, based on the polyether alcohol
water content: 0.036 wt %, based on the polyether alcohol

EXAMPLE 4

260 g of dibromoneopentyl glycol and 240 g of a reaction product of glycerol and propylene oxide having a hydroxyl number of 350 gKOH/g and an alkalinity in the form of $KH_2PO_4$ of 120 ppm, stated in terms of $K^+$ ions were fed to an autoclave having a capacity of 1 L. To this mixture there were added 2 g of boron fluoride as ethyl ether complex, the autoclave being purged with nitrogen and heated to 80° C.

At this temperature 300 g of propylene oxide were added. The aklylene oxide feed was followed by a 30 minute post reaction phase and purification. The polyether alcohol thus obtained was homogeneous and could be incorporated in conventional polyurethane systems without difficulty. It had the following specifications:
hydroxyl number: 197 mgKOH/g
viscosity at 25° C.: 1050 mPas
acid number: 0.62 mgKOH/g
pH: 5.6
bromine content: 16 wt %, based on the polyether alcohol
water content: 0.028 wt %, based on the polyether alcohol

We claim:

1. A process for the preparation of bromine-containing polyols, comprising the steps of reacting a bromine-containing alcohol with an alkylene oxide in admixture with H-functional compounds, introducing a catalyst comprising alkaline and Lewis-acid catalysts into said admixture, and thereafter separating the bromine-containing polyols from the resulting by-products, if any.

2. A process for the preparation of bromine-containing polyols as defined in claim 1, wherein the bromine-containing alcohol is an aliphatic compound having a branched carbon chain.

3. A process for the preparation of bromine-containing polyols as defined in claim 1, wherein the bromine-containing alcohol is an aliphatic compound having an unbranched carbon chain.

4. A process for the preparation of bromine-containing polyols as defined in claim 1, wherein the bromine-containing alcohol is a brominated phenol.

5. A process for the preparation of bromine-containing polyols as defined in claim 1, wherein the H-functional compound is a low molecular weight polyfunctional alcohol.

6. A process for the preparation of bromine-containing polyols as defined in claim 1, wherein the H-functional compound is a sugar alcohol.

7. A process for the preparation of bromine-containing polyols as defined in claim 1, wherein the H-functional compound is a reaction product of a polyfunctional alcohol and/or sugar alcohol with alkylene oxide.

8. A process for the preparation of bromine-containing polyols as defined in claim 1, wherein the alkaline catalyst used is an alkali metal hydroxide and/or alkali metal salt.

9. A process for the preparation of bromine-containing polyols as defined in claim 1, wherein the Lewis-acid catalyst used is boron trifluoride.

10. A process for the preparation of bromine-containing polyols as defined in claim 1, wherein the step of reacting a bromine containing alcohol with an alkylene oxide is carried out at a temperature of between about 50° to about 140° C.

11. A process for the preparation of bromine-containing polyols as defined in claim 1, wherein the step of reacting a bromine containing alcohol with an alkylene oxide is carried out at a pressure of between about 2 to about 6 bar.

12. A process for the preparation of bromine-containing polyols wherein the occurrence of side reactions and the evolution of bromine are substantially suppressed, comprising the steps of homogeneously mixing and reacting a bromine-containing alcohol, an alkylene oxide, one or more H-functional compounds and a catalyst to form a bromine-containing polyol and separating the resulting bromine containing polyol from the resulting by-products, if any.

13. A process for the preparation of bromine-containing polyols as defined in claim 12, wherein said catalyst comprises alkaline and Lewis-acid catalysts.

14. A process for the preparation of bromine-containing polyols as defined in claim 12, wherein the alkaline catalyst used is an alkali metal hydroxide and/or alkali metal salt.

15. A process for the preparation of bromine-containing polyols as defined in claim 12, wherein the Lewis-acid catalyst used is boron trifluoride.

16. A process for the preparation of bromine-containing polyols as defined in claim 12, wherein said bromine-containing alcohol is selected from the group consisting of aliphatic compounds having branched and/or unbranched carbon chains, brominated phenols and mixtures thereof.

17. A process for the preparation of bromine-containing polyols as defined in claim 12, wherein said H-functional compounds are selected from the group consisting of low molecular weight polyfunctional alcohols, sugar alcohols, reaction products of polyfunctional and/or sugar alcohols with alkylene oxides, and mixtures thereof.

18. A process for the preparation of bromine-containing polyols as defined in claim 12, wherein said steps of reacting and mixing a bromine-containing alcohol is carried out at a temperature of between about 50° to about 140° C.

19. A process for the preparation of bromine-containing polyols as defined in claim 12, wherein the step of reacting a bromine-containing alcohol, an alkylene oxide, one or more H-functional compounds and a catalyst is carried out at a pressure of between about 2 to about 6 bar.

* * * * *